(12) United States Patent
Dianaty et al.

(10) Patent No.: US 9,265,962 B2
(45) Date of Patent: Feb. 23, 2016

(54) LEADLESS INTRA-CARDIAC MEDICAL DEVICE WITH REDUCED NUMBER OF FEED-THRUS

(71) Applicant: PACESETTER, INC., Sylmar, CA (US)

(72) Inventors: Ali Dianaty, Northridge, CA (US); Gabriel A. Mouchawar, Valencia, CA (US); Gene A. Bornzin, Simi Valley, CA (US); John W. Poore, South Pasadena, CA (US); Xiaoyi Min, Thousand Oaks, CA (US); Zoltan Somogyi, Simi Valley, CA (US); Richard Williamson, Los Angeles, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 14/630,479

(22) Filed: Feb. 24, 2015

(65) Prior Publication Data
US 2015/0165221 A1    Jun. 18, 2015

Related U.S. Application Data

(62) Division of application No. 13/529,226, filed on Jun. 21, 2012, now Pat. No. 9,008,777.

(51) Int. Cl.
| | |
|---|---|
| *A61N 1/00* | (2006.01) |
| *A61N 1/375* | (2006.01) |
| *A61N 1/368* | (2006.01) |
| *A61B 5/042* | (2006.01) |
| *A61N 1/362* | (2006.01) |

(52) U.S. Cl.
CPC .............. *A61N 1/3756* (2013.01); *A61B 5/042* (2013.01); *A61N 1/362* (2013.01); *A61N 1/368* (2013.01); *Y10T 29/49002* (2015.01)

(58) Field of Classification Search
CPC ...................................................... A61N 1/375
USPC ......................................... 607/2, 35, 36, 126
See application file for complete search history.

(56) References Cited

U.S. PATENT DOCUMENTS 3,835,864 A * 9/1974 Rasor et al. ..................... 607/36

OTHER PUBLICATIONS

Restriction Requirement, mailed Mar. 11, 2014—U.S. Appl. No. 13/529,226.
NonFinal Office Action, mailed Jun. 2, 2014—U.S. Appl. No. 13/529,226.
Notice of Allowance, mailed Dec. 22, 2014—U.S. Appl. No. 13/529,226.

* cited by examiner

*Primary Examiner* — Nicole F. Lavert
*Assistant Examiner* — Nadia A Mahmood
(74) *Attorney, Agent, or Firm* — Theresa A. Raymer

(57) ABSTRACT

A leadless implantable medical device (LIMD) includes a housing formed from a battery and an end cap. A proximal end of the end cap forms an LIMD proximal end and a distal end of the battery case forms an LIMD distal end. A nonconductive coupler mechanically secures a terminal end of the battery case to a mating end of the end cap, while maintaining the battery case and end cap electrically separated. A first electrode projects from the proximal end of the end cap. An intra-cardiac (IC) device extension projects from the distal end of the battery case. The extension includes a second electrode that is electrically connected to the battery case. The second electrode is located remote from the LIMD distal end. An electronics module is located within an internal cavity of the end cap and communicates with the first and second electrodes.

10 Claims, 8 Drawing Sheets

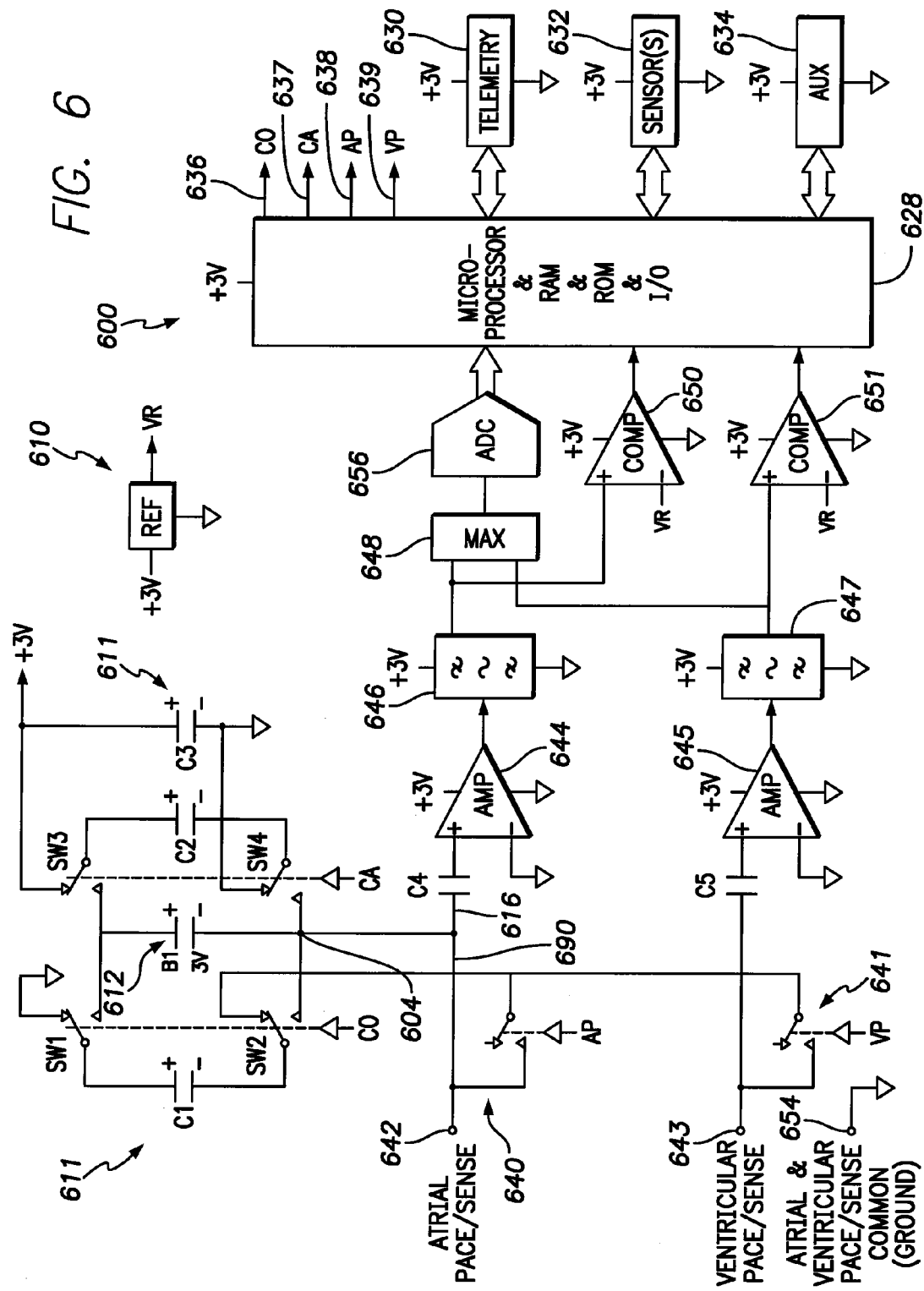

LEADLESS INTRA-CARDIAC MEDICAL DEVICE WITH REDUCED NUMBER OF FEED-THRUS

CROSS REFERENCE TO RELATED APPLICATIONS

This application is a division of U.S. patent application Ser. No. 13/529,226, filed Jun. 21, 2012.

FIELD OF THE INVENTION

Embodiments of the present invention generally relate to leadless implantable medical devices, and more particularly to leadless intra-cardiac medical devices with a reduced number of feed-thrus. As used herein, the term "leadless" generally refers to an absence of electrically-conductive leads that traverse vessels or other anatomy outside of the intra-cardiac space, while "intra-cardiac" means generally, entirely within the heart and associated vessels, such as the SVC, IVC, CS, pulmonary arteries and the like.

BACKGROUND OF THE INVENTION

Currently, permanently-implanted pacemakers (PPMs) utilize one or more electrically-conductive leads (which traverse blood vessels and heart chambers) in order to connect a canister with electronics and a power source (the can) to electrodes affixed to the heart for the purpose of electrically exciting cardiac tissue (pacing) and measuring myocardial electrical activity (sensing). The leads may experience certain limitations, such as incidences of venous stenosis or thrombosis, device-related endocarditis, lead perforation of the tricuspid valve and concomitant tricuspid stenosis; lacerations of the right atrium, superior vena cava, and innominate vein or pulmonary embolization of electrode fragments during lead extraction.

A small sized PPM device has been proposed with leads permanently projecting through the tricuspid valve and that mitigate the aforementioned complications. Optionally, an entire PPM with lead may be in atrium only and not have a lead projecting through the tricuspid valve. The PPM is a reduced-size device, termed a leadless implantable medical device (LIMD), characterized by the following features: electrodes are affixed directly to the can of the device; the entire device is attached to the heart.

The LIMD are able to sense in one or two chambers and deliver pacing pulses in the same chambers. For example, an LIMD may be located in the right atrium to offer various mode functionality. An AAI mode LIMD typically only senses in the right atrium, paces in the right atrium, and inhibits pacing function when an intrinsic event is detected in the right atrium within a preset time limit. Similarly, an LIMD may be located in the right ventricle to offer various mode functionality. A VVI mode LIMD typically only senses in the right ventricle, paces in the right ventricle, and inhibits pacing function when an intrinsic event is detected in the right ventricle within a preset time limit.

Optionally, a DDD mode LIMD may be located in the right atrium or right ventricle. The DDD mode LIMD may include a stabilizing intra-cardiac (IC) device extension that has an electrode provided thereon. The LIMD with the IC device extension collectively provide pacing and sensing in the RA and RV and inhibit pacing when an intrinsic event is detected.

However, the LIMDs proposed thus far exhibit certain limitations. For example, LIMDs include multiple components within the housing that limit the degree to which cost and size can be reduced. For example, LIMDs include an electronics module, battery and multiple feed-thrus within the housing. The feed-thrus afford interfaces for conductors to leave and enter a hermetically sealed chamber or area within the LIMD. As one example, LIMDs utilize a feed-thru between the interior of the housing and the leads that carry at least one electrode to pace/sense in the RA. LIMDs utilize another feed-thru between the battery and the electronics module. The use of multiple feed-thrus increases the cost and size of the LIMD. A need remains or an LIMD design that utilizes fewer feed-thrus and decreases the size and cost of the LIMD.

SUMMARY

In accordance with one embodiment, a leadless implantable medical device (LIMD) is provided that is configured to be implanted within a chamber of the heart. The LIMD comprises a housing formed from a battery and an end cap. The battery has a battery case with a distal end and a terminal end. The end cap has an open end and a proximal end. The proximal end of the end cap forms an LIMD proximal end and the distal end of the battery case forms an LIMD distal end. A non-conductive coupler mechanically secures the terminal end of the battery case to the open end of the end cap, while maintaining the battery case and end cap electrically separated from one another. A first electrode is joined to the proximal end of the end cap, projects from the LIMD proximal end and is configured to engage tissue of interest at a first activation site. A second electrode is provided and is connected to the battery case with the battery case forming part of the circuit that connects the second electrode to sensing and/ or pacing components to sense or stimulate tissue of interest at a second activation site.

An intra-cardiac (IC) device extension may be used that projects from the distal end of the battery case. The IC device extension includes the second electrode that is electrically connected to the battery case. The second electrode is located remote from the LIMD distal end and is configured to engage tissue of interest at a second activation site.

An electronics module is located within an internal cavity of the end cap and communicates with the first and second electrodes to perform at least one of sensing and therapy delivery.

The battery includes first and second terminals connected to the electronics module, with the first terminal electrically common with the battery case and the second electrode. The electronics module utilizes the end cap as a common electrode and delivers therapy to atrial tissue of interest between the second electrode and the end cap with the second electrode forming a cathode and the end cap forming an anode.

Optionally, the electronics module may utilize the end cap as a common electrode and deliver therapy to ventricular tissue of interest between the first electrode and the end cap with the first electrode forming a cathode and the end cap forming an anode.

In accordance with one embodiment, a charge storage unit is provided having anode and cathode terminals, with the electronics module connecting the cathode terminal to the battery case and first electrode, and connecting the anode terminal to the end cap when delivering therapy to the first activation site. Optionally, an insulation coating surrounds the battery case to isolate the battery case electrically from heart tissue. A wire directly connects the battery case to the second electrode located distal from the LIMD. The IC device extension includes an elongated body having a base and an outer end, the base mounted to the distal end of the battery case, and the second electrode located at the outer end. The non-conductive coupler has opposed edges that are bonded to, and electrically isolate, the battery case and the end cap from one another. The battery case is electrically common with the second electrode and forms a cathode during therapy delivery.

The non-conductive coupler may constitute one of a sapphire, ceramic or other hermetic insulation ring having opposed circumferential edges that are bonded to corresponding edges on the terminal end of the battery case and the open end of the end cap. The battery case constitutes an LIMD exterior housing.

In accordance with one embodiment, a method is provided for providing a LIMD configured to be implanted within a chamber of the heart. The method comprises forming a housing from a battery and an end cap, the battery having a battery case with a distal end and a terminal end, the end cap having an open end and a proximal end, the proximal end of the end cap forming an LIMD proximal end and the distal end of the battery case forming an LIMD distal end. The method mechanically secures the terminal end of the battery case to the open end of the end cap with a non-conductive coupler, while maintaining the battery case and end cap electrically separated from one another. The method joins a first electrode to the proximal end of the end cap, the first electrode oriented to project from the LIMD proximal end and configured to engage tissue of interest at a first activation site. The method attaches an IC device extension to the distal end of the battery case, the IC device extension including a second electrode that is electrically connected to the battery case. The second electrode is located remote from the LIMD distal end and is configured to engage tissue of interest at a second activation site. The method utilizes the first and second electrodes to perform at least one of sensing and therapy delivery under control of an electronics module within an internal cavity of the end cap.

In accordance with one embodiment, the method connects first and second terminals of the battery to the electronics module such that the first terminal is electrically common with the battery case and the second electrode. The method utilizes the end cap as a common electrode and delivers therapy to atrial tissue of interest between the second electrode and the end cap, with the second electrode forming a cathode and the end cap forming an anode. The method utilizes the end cap as a common electrode and delivers therapy to ventricular tissue of interest between the first electrode and the end cap with the first electrode forming a cathode and the end cap forming an anode. The method connects the cathode terminal to the battery case and first electrode when delivering therapy to the first activation site.

Optionally, the method surrounds the battery case with an insulation coating to isolate the battery case electrically from heart tissue.

BRIEF DESCRIPTION OF THE DRAWINGS

FIG. 6 illustrates a schematic diagram of an LIMD such as a DDDR leadless pacer (LLP).

DETAILED DESCRIPTION

Figure 1A:
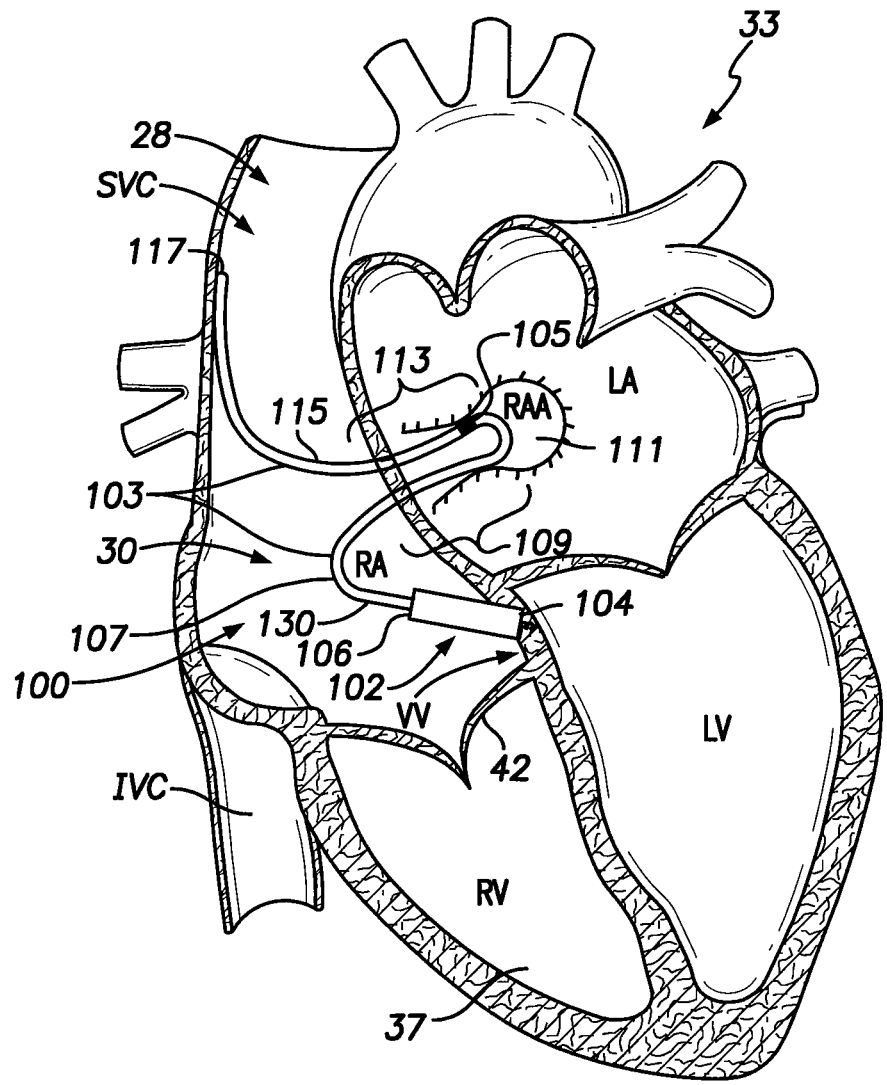
FIG. 1A illustrates a sectional view of a patient's heart and shows an LIMD.

FIG. 1A illustrates a sectional view of a patient's heart 33 and shows an LIMD 100. The LIMD 100 may have been placed through the superior vena cava (SVC) 28 or inferior vena cava (IVC) into the right atrium 30 of the heart 33. The LIMD 100 comprises a housing 102 configured to be implanted entirely within a single local chamber of the heart. The housing 102 includes a proximal base end 104 and a distal top end 106. The proximal base end 104 includes an active fixation member, such as a helix, that is illustrated to be implanted in the ventricular vestibule (W). A shaped intracardiac (IC) device extension 103 extends from the distal top end 106 of the housing 102. The IC device extension 103 comprises an elongated body that may be tubular in shape and may include a metal braid provided along at least a portion of the length therein. The extension body may include a transition sub-segment, an active interim-segment and a stabilizer end-segment, all of which are illustrated in a deployed configuration. For example, the active interim-segment (e.g., second curved segment 111, and all or portions of the first and second linear regions 109 and 113) and the stabilizer end-segment (e.g., third curved segment 115 and all or portions of the second linear region 113) are shown preloaded against anatomical tissue of interest. One or more electrodes 105 are carried by the IC device extension 103 and are electrically connected to electronics within the housing 102 through conductors extending through the body of the IC device extension 103.

Figure 1B:
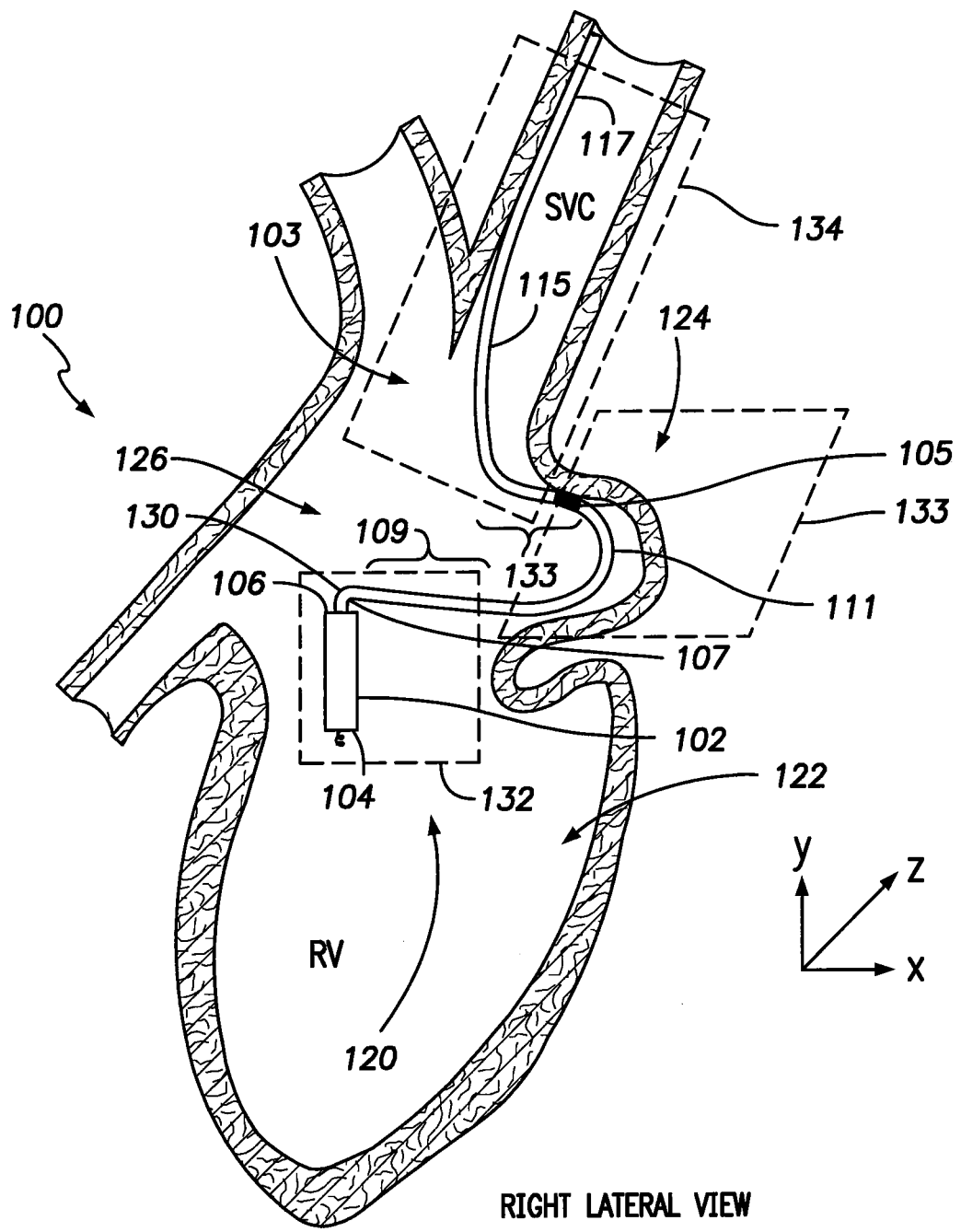
FIGS. 1B and 1C further illustrate a model of an interior of a human heart and shows an example of the LIMD having the shaped IC device extension described with reference to FIG. 1A.
Figure 1C:
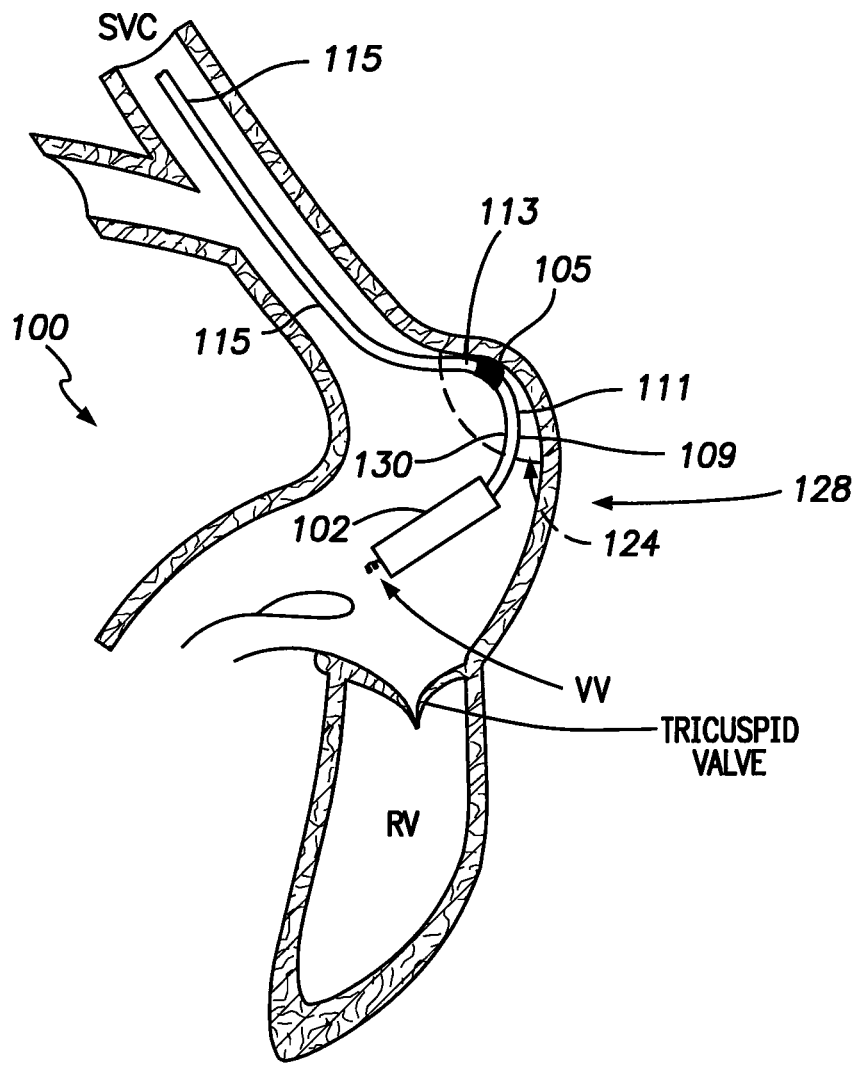

The IC device extension 103 forms a stabilizing mechanism to assist in holding the LIMD 100 in place. The IC device extension 103 is formed with shape memory characteristics that allow the IC device extension 103 to transform between a collapsed state, in which the IC device extension 103 assumes a substantially linear shape, and an expanded state, in which the IC device extension 103 assumes a multiple curved shape, such as shown in FIGS. 1A-1C. In one embodiment, the curved configuration of the IC device extension 103 comprises multiple sharply curved segments, obtusely curved segments, generally linear regions and the like. The number, length, and order of the segments and regions, as well as the degree to which individual segments or regions are curved or linear may vary depending upon the anatomical contour to be followed.

The IC device extension 103 includes a short stem 130 that extends a short distance from the distal top end 106 of the housing 102. The stem 130 merges into a first curved segment 107 that turns at a sharp angle with respect to a longitudinal axis of the housing 102. Optionally, the first curved segment 107 may form an acute angle, 90 degree angle, or obtuse angle approximately with respect to a longitudinal axis of the housing 102. The first curved segment 107 merges into and is followed by a first generally linear region 109 that extends laterally from the housing 102, along a lateral axis, until merging with a second curved segment 111. The second curved segment 111 turns at a sharp angle with respect to the longitudinal axis of the housing 102 and the lateral axis of the first linear region 109.

One or more electrodes 105 are located along the second curved segment 111. Optionally, the electrode(s) may be provided in the region proximate to the junction of the second curved segment 111 and the second linear region 113. Optionally, one or more electrodes 105 may be provided along the second linear region 113.

The second linear region 113 merges with and extends to a third curved segment 115. The third curved segment 115 follows an extending "slow" arc and then terminates at a tail end 117 of the IC device extension 103.

The shaped IC device extension 103 is formed into a preloaded shape in which the first, second and third curved segments 107, 111 and 115 extend along desired arcuate paths and project from longitudinal/lateral axes at desired pitch, roll and yaw angles, where the pitch, roll and yaw angles are measured from reference angular positions.

With continued reference to FIG. 1A, the LIMD 100 is configured to place the housing 102 in the lower region of the right atrium between the OS and inferior vena cava (IVC) with a distal helix electrode, on the housing 102, in the ventricular vestibule (VV) to provide ventricular pacing and sensing. The IC device extension 103 extends upward in the right atrium toward and into the superior vena cava (SVC). The IC device extension 103 is configured (length wise and shape wise) such that the second curved segment 111 may be implanted within the right atrial appendage (RAA), along with those portions of the first and second linear regions 109, 113 near the second curved segment 111. The configuration in FIG. 1A places the electrode 105 in the RAA to allow for right atrial pacing and sensing. The configuration in FIG. 1A also places the proximal portion of the third curved segment 115 against a wall of the SVC to provide overall stability to the LIMD 100.

FIGS. 1B and 1C further illustrate a model of an interior of a human heart and shows an example of the LIMD 100 having the shaped IC device extension 103 described with reference to FIG. 1A. FIG. 1B generally illustrates an exemplary right lateral view of a heart, while FIG. 1C generally illustrates an exemplary anterior-posterior (AP) view. As points of reference, the RV vestibule 120, RAA 124, and RV outflow track 122 are illustrated in one or both of FIGS. 1B and 1C. The AP view of FIG. 1C is oriented relative to the right lateral view of FIG. 1C, such that the viewer's line of sight (in FIG. 1C) is directed into the RAA 124 along arrow 126 in FIG. 1B, whereas the viewer's line of sight in FIG. 1B is directed in the direction of arrow 128 in FIG. 1C.

The LIMD 100 is shown to be actively affixed near the RV vestibule 120. The views illustrated in FIGS. 1B and 1C are merely exemplary models of a potential three dimensional shape of the IC device extension 103. To further illustrate the 3D geometry of the IC device extension 103, planes 132-134 are shown in dashed line. The plane 132 generally follows X and Y axes that are defined with respect to the orientation of the housing 102. For example, the Y axis may correspond to the longitudinal axis of the housing 102. The plane 133 generally follows X and Z axes, wherein the X axis is oriented laterally with respect to the longitudinal axis of the housing 102 (e.g., from left to right across the drawing sheet). The Z axis is oriented transversely with respect to the longitudinal axis of the housing 102 and the lateral X axis (e.g., in and out of the drawing sheet).

Optionally, the IC device extension 103 may have other shapes such as a forked two piece arrangement with an electrode support arm and a stabilization member. Optionally, the IC device extension 103 may have multiple electrodes provided along the body, where the multiple electrodes are electrically separated or electrically common.

FIGS. 1A, 1B and 1C illustrates an LIMD 100 that is configured to reduce the number of feed-thrus needed for ventricular and atrial pacing and sensing from an LIMD, such as a DDD leadless pacer. As explained herein, the LIMD 100 only includes a single feed-thru, whereas conventional LIMD designs needed at least two feed-thrus. In one embodiment, the LIMD 100 is positioned in the RA floor between the OS and SVC to access ventricular tissue for V pace/sense.

In certain embodiments, ventricular pacing electrodes are formed as an anodal helix and cathodal center pin. The ventricular sensing electrode configurations described herein are configured to reject atrial far field signals by affording a small spacing between the cathodal pin electrode and the anodal helix electrode.

For example, the anodal helix electrode may be connected to the metal housing of the LIMD 100 to eliminate the use of a feed-thru to provide electrical contact between the anodal helix electrode and the electronics within the LIMD 100. The device housing may be electrically separated into segments through the use of an insulated connection joint or coupler that is positioned between the main body (which holds the battery) and the end cap (which holds the electronics and ring shaped insulated electrode supports). The insulation over the battery case exterior may be optional when the atrial electrode is connected to the battery. In certain embodiments, the battery case may be coated with insulation material and the segment (or the atrial tail) of atrial pacing/sensing is connected to the end cap, in order to eliminate the need of a feed-thru for the atrial tail. The end cap for pacer electronics is electrically connected to ventricular anodal helix and it is also the anode for atrial pacing/sensing electrode. The end cap for the electronics can be fully or partially insulated or not. For example, the end cap may be covered with insulation all but a 1 mm area of the end cap near the helix in order to get a better pacing threshold. This DDD leadless pacer would only use one feed-thru for a ventricular cathode, which greatly reduces the cost.

Figure 2:
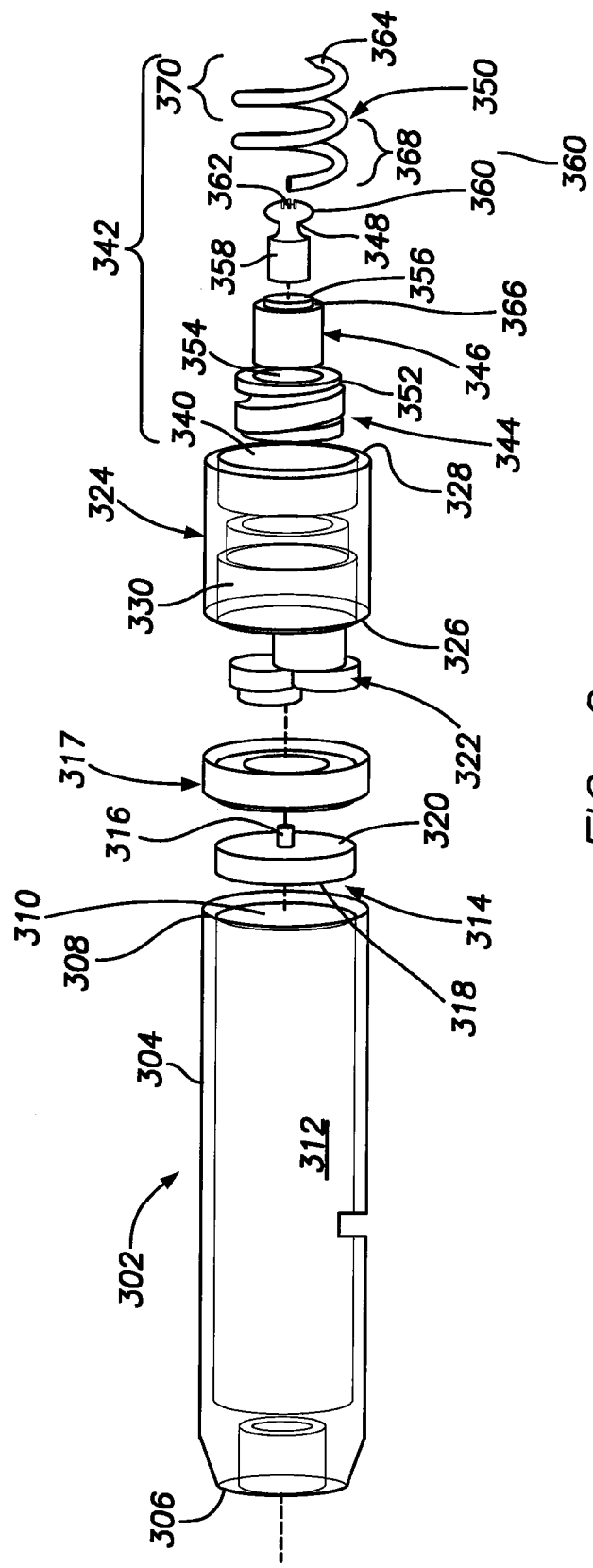
FIG. 2 illustrates an exploded view of an LIMD formed in accordance with an embodiment of the present invention.
Figure 3:
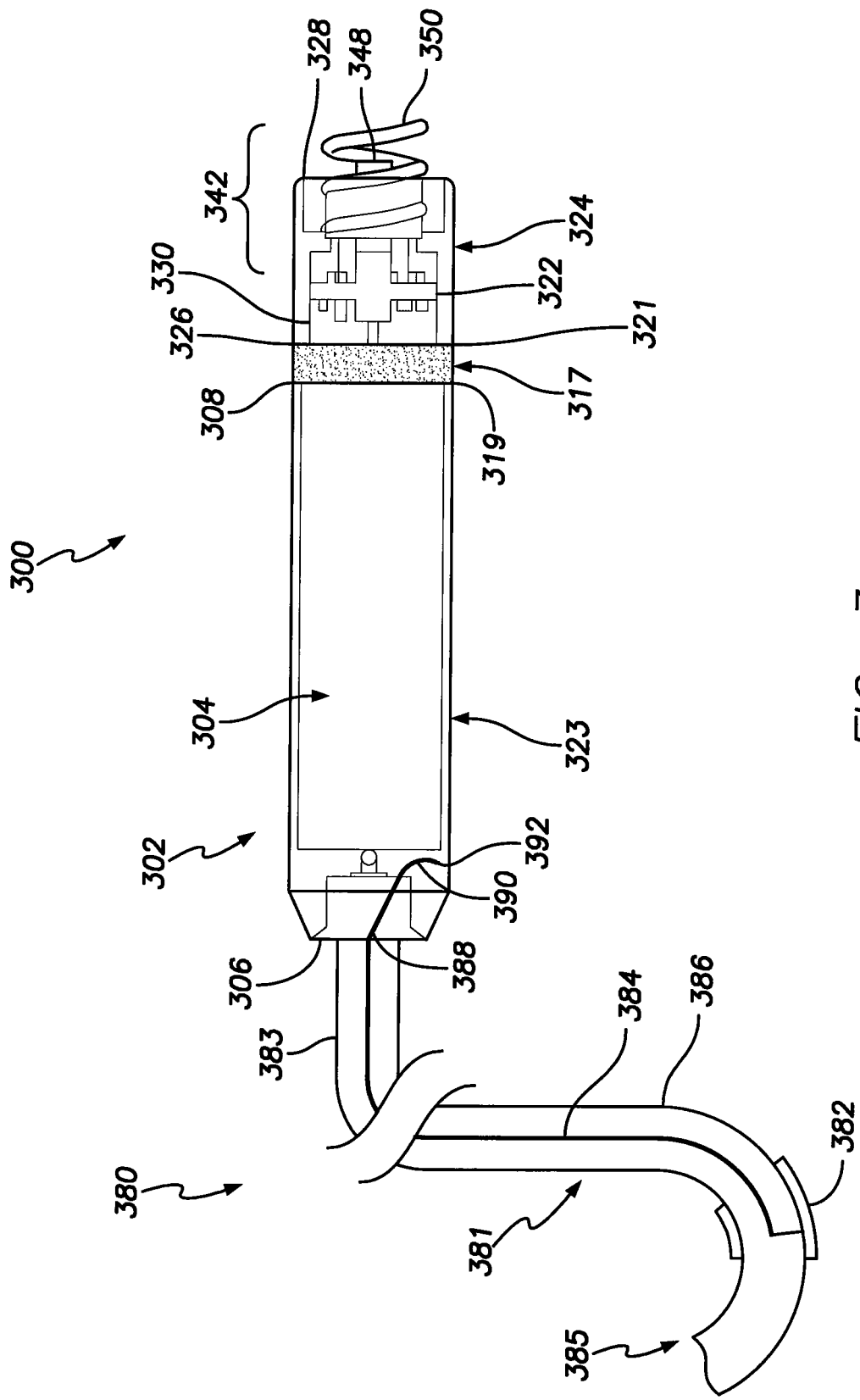
FIG. 3 illustrates a side view of the LIMD.

FIGS. 2 and 3 illustrate an LIMD 300 formed in accordance with an embodiment. The LIMD 300 includes a housing that is formed from a battery 312 and an end cap 324. The battery has a battery case 304 with a closed distal end 306 and an open terminal end 308. The end cap 324 has a mating open end 326 and a proximal end 328. The end 326 may be open or at least partially closed. The proximal end 328 of the end cap 324 defines and forms the proximal end of the overall LIMD 300. The terms proximal and distal shall be used throughout with respect to the end of the LIMD 300 that is secured to and engages tissue of the heart. Hence, structures near the point of tissue engagement shall be proximal and structures remote from tissue engagement shall be distal. The distal end 306 of the battery case 304 defines and forms the distal end of the overall LIMD 300.

A nonconductive coupler 317 is positioned between and bonded to the terminal end 308 of the battery case 304 and to the mating open end 326 of the end cap 324. The coupler 317 mechanically secures the battery case 304 to the end cap 324, while also maintaining the battery case 304 and end cap 324 electrically separated from one another. The coupler 317 may be formed from various materials that are nonconductive, bio-compatible and afford a secure mechanical connection between the battery 302 and end cap 324. For example, the coupler 317 may be formed from sapphire, ceramic and the like. The coupler 317 has opposed circumferential edges 319 and 321 that are bond to mating edges of the terminal end 308 and open end 326. For example, a bonding agent, such as gold or some other material, may be provided between the coupler 317, end cap 324 and battery case 304 to facilitate bonding to the corresponding edges 319 and 321. The coupler 317 is ring-shaped with an outer diameter that substantially conforms to the outer diameter of the battery case 304 and end cap 324. The coupler 317 has an inner diameter that also substantially matches the inner diameter of the battery retention cavity 310 (FIG. 3) and the cavity 320 within the end cap 324.

The end cap 324 retains an electrode subassembly 342 which includes, among other things, an anode electrode 350 and a cathode electrode 348. The electrode subassembly 342 is coupled to an electronics module 322. The cathode electrode 348 is joined to the proximal end 328 of the end cap 324 and projects from the proximal end of the overall LIMD 300. The cathode electrode 348 is configured to engage tissue of interest at a first activation site.

An IC device extension 380 is provided that is attached to the distal end 306 of the LIMD 300. The IC device extension 380 projects from the distal end 306 of the battery case 304 and includes at least one additional electrode 382 at a desired point along the length thereof. The electrode 382 is connected to a conductor 384 that extends along a lumen 386 that extends along a portion of the length and is within the IC device extension 380. The conductor 384 is joined at a connection point 388 to a linking conductor 390 which is attached at the opposite end 392 to the battery case 304. The linking conductor 390 renders the conductor 384 and battery case 304 electrically common, and thus renders the battery case 304 as part of a circuit that connects the electrode 382 to the electronics module 322, for sensing operations and/or for delivering therapy. The electrode 382 is located remote from the distal end 306 of the battery case 304 and is configured to engage tissue of interest at a second activation site (such as in the right atrial appendage) that is remote from the first activation site at which the electrode 348 engages tissue. The first and second activation sites may be associated with different chambers such as ventricular and atrial tissue, respectively.

An electronics module 322 is located within an internal cavity 330 within the end cap 324. The electronics module 322 communicates with the electrodes 382, 348, 350, as well as with the end cap 324 in order to perform sensing and to deliver therapy.

As explained below in more detail, the electronics module 322 utilizes the end cap 326 which may be fully or partially insulated and is permanently connect to the helix electrode 350 to avoid another feed-thru. The end cap 326 and helix electrode 350 are a common electrode and delivers therapy to tissue of interest between the electrode 382 and the end cap 324. For example, the electronics module 322 may control a switching circuit therein to render the electrode 382 to operate as a cathode and the end cap 324 to operate as an anode, between which therapy is delivered. As a further option, the electronics module 322 may control the switching circuit to utilize the electrode 348 and electrode 350 to deliver a therapy to tissue at an activation site proximate thereto, with the electrode 348 operating as a cathode, while electrode 350 operates as an anode. Optionally, a therapy may be delivered utilizing the electrode 348 as a cathode and the end cap 324 as the anode.

The battery case 304 is enclosed within an insulated coating 323 to isolate the battery case 304 electrically from the heart tissue. Optionally, when an additional electrode is desired to be provided in an area surrounding the battery case 304, portions of the insulated coating 323 may be omitted in order to expose portions of the battery case 304 to the heart tissue and thereby provide the battery case 304 as an additional electrode, such as when there is no atrial tail electrode.

The IC device extension 380 includes an elongated body 381 having a base 383 and an outer end 385. The base 383 is mounted to the distal end 306 of the battery case 304. The second electrode 382 is provided proximate to the outer end 358. The elongated body 381 includes the lumen 386, along which the conductor 384 extends between the electrode 382 and the linking conductor 390.

FIG. 3 illustrates a view of the LIMD 300. The LIMD 300 includes two segments, one of which constitutes a tubular shaped main body 302 which forms the battery case 304 with a closed distal end 306 and an open proximal end 308. The open proximal end 308 opens onto an electrolyte retention cavity 310 which is configured to hold a battery electrolyte 312. The proximal end 308 also receives a disc shaped battery feed-thru 314 which has generally flat opposed inner and outer surfaces 318 and 320. The electrolyte is received through a hole in the distal end 306. The hole is then closed with a ball bearing. End 308 is used to insert the battery electrode/separator material prior to welding the battery feedthrough 314 on after which the electrolyte is injected into the distal end 306. The inner surface 318 is configured to abut against a facing end of the cavity 310. The outer surface 320 is configured to abut against an electronics module 322. The battery feed-thru 314 includes one or more contact pins 316 that extend through the feed-thru. The contact pins 316 have inner ends that are configured to engage the electrolyte 312. The contact pins 316 also have outer ends that extend from the outer surface 320 and are configured to align with and electrically couple to mating contacts on the electronics module 322.

In the example of FIG. 3, the end cap 324 is tubular in shape and has open opposed ends 326 and 328. The end 326 opens onto an internal cavity 330 within the end cap 324. The cavity 330 is dimensioned to retain the electronics module 322. The end 328 opens onto an internal cavity 340 that is dimensioned to retain an electrode subassembly 342. The electrode subassembly 342 includes a helix support/insulator 344, a cathode support/insulator 348, the cathode electrode 348 and the anode electrode 350. In the example of FIG. 3, the cathode electrode 348 is shaped as a pin. The anode electrode 350 is formed in a helix or spiral configuration with a predetermined diameter and having an outer tip 364 that is configured to be securely affixed to tissue of interest. Optionally, the electrodes 350 and 348 may have other shapes.

The support/insulator 344 is formed with a spiral-shaped groove 352 that is dimensioned to correspond to the diameter and spiral pitch of the anode electrode 350. The groove 352 wraps about the perimeter of the support 344. The support 344 also includes an internal passage 354 that is dimensioned with an inner diameter corresponding to the outer diameter of the cathode support 346. The cathode support 346 is slidably received within the passage 354 within the anode support 344. The cathode support 346 further includes an internal passage 356 that is shaped and dimensioned to receive a base section 358 of the cathode electrode 348. The cathode electrode 348 includes a base segment 358 that is formed integral with a tip section 360 that is flared outward to provide a desired amount of electrode active area to engage the tissue of interest. Optionally, the tip 360 may include a number of projections 362 to facilitate the coupling of the cathode electrode 348 and the tissue.

The LIMD configurations discussed herein eliminate a feed-thru in connection with the remote electrode on the IC device extension. Stated another way, the electrical path between the electrode 105 or 382 and the battery avoids or lacks a feed-thru.

Optionally, the locations of the IC device extension 380 and the electrodes 348 and 350 may be reversed relative to the battery 312 and electronics 322. For example, the electrodes 348 and 350 may be positioned proximate to the battery 312

(e.g. at end 306), while the IC device extension 380 is positioned proximate to the electronics 322 (e.g., at end 328).

Figure 4:
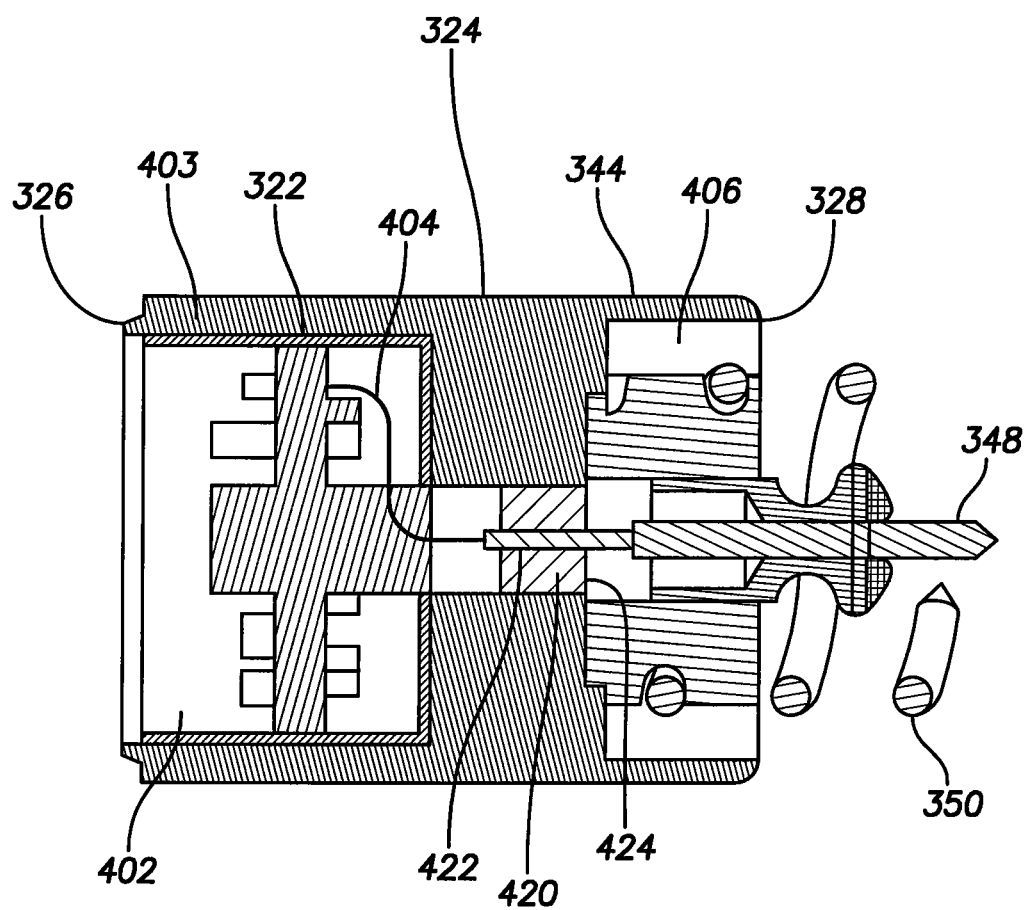
FIG. 4 illustrates a cross section view of the end cap with the corresponding components loaded therein.

FIG. 4 illustrates a cross sectional view of the end cap 324 with the corresponding components loaded therein. The end cap 324 has an open interior channel extending between the first open distal end 326 and the proximal end 328. The channel 402 is comprised of an insulated chamber 403. The chamber contains the feed-thru and electronics. The insulated chamber 403 receives the battery feed-thru 314 when loaded through the distal end 326. The chamber 403 also receives the electronics module 322 when loaded through the distal end 326. The chamber 403 also receives the electronics module 322 when loaded through the distal end 326. The retention chamber 406 receives the anode and cathode supports 344 and 346 when loaded through the proximal end 328.

The interior channel through the end cap 324 is formed with ledges to control the alignment of various components within the end cap 324.

The end cap 324 retains the anode support 344, cathode support 346, cathode electrode 348 and anode electrode 350 in a concentric arrangement, and at least partially exposed from the proximal end 328. The internal passage 356 of the cathode support 348 holds the cathode electrode 348. The external groove 352 that wraps about the anode support 344 supports and retains the anode electrode 350.

An electrode feed-thru 420 is held within the end cap 324 between the electronics and electrode retention chambers 402 and 406. The electrode feed-thru 420 forms a sealed a barrier between the electronics and electrode retention chambers 402 and 406. A conductive pin or wire 422 extends between opposite sides 424 and 426 of the electrode feed-thru 420 to carry electrical signals (e.g. sensing signals or stimulus pulses) between the electronics and electrode retention chambers 402 and 406 respectively. Connection wire 404 from tip of feed-thru conductor 422 connects electrode 348 to the electronics-module 322.

The anode electrode 350 includes a base segment 368 and a tissue engaging segment 370. The base segment 368 wraps about the anode support 344 and follows the groove 352. The tissue engaging segment 370 projects beyond the outer surface 366 of the anode support 344.

Figure 5:
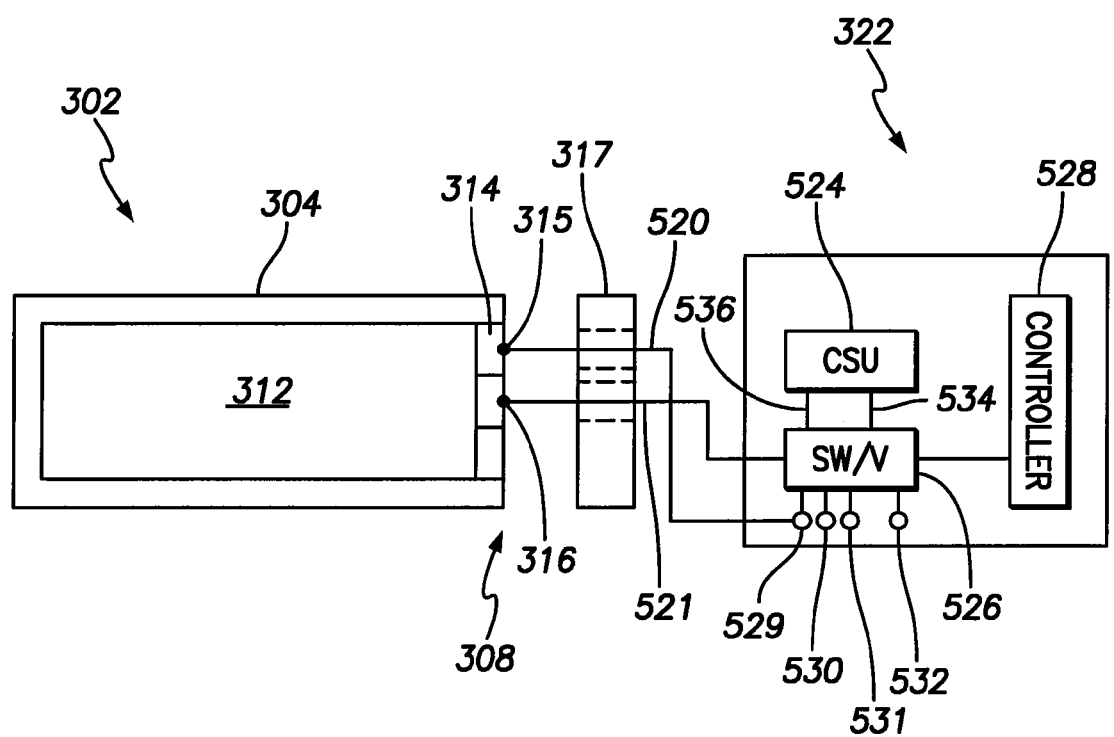
FIG. 5 illustrates a schematic representation of a portion of electrical pathways and inter-connections within the LIMD.

FIG. 5 illustrates a schematic representation of a portion of electrical pathways and inter-connections within the LIMD 300. In FIG. 5, the battery case 304 is illustrated with the interior cavity configured to receive battery components 312 to form the battery. The feed-thru 314 is provided at the open end 308. Terminals 316, 315 are provided on the battery 302 to afford an electrical potential therebetween corresponding to the voltage potential generated by the battery 302. Terminals 315, 316 are connected by lines 520, 521 to a switch unit 526 provided on the electronics module 322. The electronics module 322 further includes a charge storage unit 524 and a controller 528. The charge storage unit 524 is connected to the switch unit 526 through lines 534, 536.

During a charging operation, under the control of the controller 528, the switch unit 526 connects lines 534, 536 with lines 520, 521 to charge up the charged storage unit 524. When it is determined that a therapy is to be delivered, the controller 528 causes the switch unit 526 to connect lines 534, 536 to select combinations of switch output terminals 529-532. In the example of FIG. 5, the switch unit 526 includes four output terminals 529-532; however alternatively more or fewer output terminals may be provided. The output terminals 529-532 are connected to corresponding electrodes depending upon the configuration and implant site for the LIMD 300. By way of example, terminal 529 may be connected over line 521 back to the battery case 304. Terminal 530 may be connected to the end cap 324, thereby forming an anode that may be used during sensing and/or delivery of therapy. Terminals 531, 532 are connected to electrodes 348, 350 (FIG. 3) and may be used during one or both of sensing and therapy delivery. As shown in FIG. 5, the battery case 304 is electrically common with the terminal 315 as well as the electrode 382 (FIG. 2).

The charge storage unit 524 has anode and cathode terminals, corresponding to lines 534, 536. The electronics module 322 connects the anode and cathode terminals to select electrodes based upon the therapy and configuration. For example, the electronics module 322 may connect the cathode terminal (one of 534 and 536) to the battery case 304 through output terminal 529 and line 521, thereby similarly connecting the cathode terminal to the electrode 382 when delivering therapy to the corresponding activation site. The electronics module 322 may further connect an anode terminal to the end cap 324 when delivering therapy to the first activation site.

FIG. 6 illustrates a schematic diagram of an LIMD such as a DDDR leadless pacer (LLP) 600. The LLP 600 uses the battery case (e.g. 304 in FIG. 2) as an electrical conductor to connect an atrial pace/sense electrode (e.g. electrode 382 in FIG. 3 or 105 in FIG. 1A) to the pace/sense electronics within the LLP 600. By utilizing the battery case as an electrical conductor, this obviates the need for an atrial electrode feed-thru that would otherwise be used to connect the electronics of the LLP 600 to the external atrial electrode. In FIG. 6, the battery case represents the negative terminal of the battery 611. Optionally, the battery case may instead be implemented as the positive terminal, based upon the type of electrolyte provided within the battery 611.

In FIG. 6, the battery 612 is connected to a network of switches SW1, SW2, SW3, and SW4. The switches SW1-SW4 connect the battery 612 to a group of capacitors C1-C3 that collectively form a charge storage device 611. The switches SW1-SW4 are controlled by control lines C0 and CA (also referred to as 636 and 637) which are output from a microcontroller 628. The microcontroller 628 also communicates with telemetry circuitry 630, sensor circuits 632, auxiliary circuitry 634 and the like. The microcontroller 628 has output control lines 636-639 that control the switches SW1-SW4 and therapy delivery switches 640, 641. Switches 640, 641 are coupled to electrode terminals 642, 643 which are in turn connected to corresponding electrodes, such as the electrode 105 (FIG. 1A), electrode 382 and electrode 348 (FIG. 3). As one example, the terminal 642 may be connected to an atrial pace/sensing electrode, while terminal 643 may be connected to a ventricular pace/sense electrode.

The switches 640, 641 are closed when the LLP 600 determines that it is time to deliver a therapy to the corresponding chamber of the heart. When it is desirable to deliver an atrial pacing pulse, switch 640 changes position to connect terminal 642 to the atrial pace/sense electrode. Similarly, when it is desirable to deliver a ventricular pacing pulse, switch 641 connects terminal 643 to the charge storage device 611 to thereby deliver a therapy to the ventricular chamber.

During sensing windows, the switches 640, 641 are in the positions shown in FIG. 6. During sensing, electrical signals detected at the corresponding electrodes are supplied from terminals 642, 643 to amplifiers 644, 645. The input signals to amplifiers 644, 645 are compared to a reference or ground potential. The reference or ground potential is common with the potential at output terminal 654 which is connected to the end cap (e.g. end cap 324) or some other electrode that is used as a common anode electrode. The amplifiers 644, 645 provide sensed signals that are passed through filters 646, 647 to further process the sensed signals. The sensed filtered signals output from filters 646, 647 are supplied to a multiplexer 648 and to comparators 650, 651. the comparators 650, 651 compare the incoming filtered sensed signals to a reference voltage and determine if the signals are greater than or less than the reference; the corresponding output is logical one if the signal is greater and logical zero if lower. Hence, comparator 650 compares the reference voltage to the signals sensed at the atrial pace/sensed electrode (corresponding to terminal 642). The comparator 651 compares the reference voltage to the signals sensed at the ventricular pace/sensed electrode (corresponding to terminal 643). The signals output from comparator 650, 651 are then analyzed by the microcontroller 628 to monitor activity within the corresponding chambers of the heart.

The multiplexer 648 switches between the filtered signals supplied from filters 646, 647 to provide the select one of the incoming signals to an analog to digital converter 656 which then digitizes the selected signal.

Node 604 corresponds to the battery case (e.g. battery case 304 in FIG. 2). The node 604 is connected by a linking wire 690 to the terminal 642. The node 604 is connected through linking conductor 616 to the sense amplifier 644. The links 690, 616 may correspond to the linking conductor 390 in FIG. 3 and the contact pin 316 in FIG. 2. Hence, the atrial pace/sense electrode is directly connected to the negative terminal (through node 604) of the battery 612. The switches SW3 and SW4 produce a three-volt power supply on capacitor C2 that is isolated from the battery 612 when the control signal at line CA is set to a logical low or zero. The voltage on capacitor C2 is transferred to capacitor C3 during this time period to produce a three-volt power supply that is utilized by the LLP 600 as the ground referenced power supply (as illustrated at 670). As noted above, the ground reference is also utilized as the atrial and ventricular pace/sense common electrode. As one example, the common electrode may be the end cap 324. When the control signal CA is changed to a logical high or one, the capacitor C2 is charged by the battery to three-volts by connecting both sides of the capacitor C2 to the battery, while the capacitor C3 continues to provide power to the LLP 600.

Similarly, the switches SW1 and SW2 produce a three-volt power supply onto capacitor C1 that is isolated from the battery 612 when the control signal C0 is set to a logical low or zero. While control signal C0 is set to logical zero, the voltage on capacitor C1 is available to be used to generate a negative atrial or ventricular pacing voltage. The voltage on capacitor C1 is supplied as a negative atrial or ventricular pacing voltage when the corresponding one of the atrial or ventricular pacing control signals AP or VP is respectively pulsed to close the corresponding one of switches 640, 641. When control signal C0 is set to a logical high or one, the capacitor C1 begins to charge from the battery up to three-volts given that control signal C0 switches the position of switches SW1 and SW2 to connect the battery 612 to the capacitor C1.

The three-volt power supply provided by the capacitor C3 is used to provide power to all of the electronics within the LLP 600, such as the atrial sense amplifier 644, ventricular sense amplifier 645, atrial filter 646, ventricular filter 647, multiplexer 648, A-D converter 656, atrial sense comparator 650, ventricular sense comparator 651, microprocessor 628, any RAM, ROM, input, output electronics, telemetry circuitry 630, sensor circuitry 632 and other auxiliary circuitry 634.

While the example of FIG. 6 represents a simplified LLP 600, it is recognized that additional programming options may be provided. Although FIG. 6 shows the negative terminal of the battery as the battery case, the schematic could be easily reconfigured to have the positive terminal of the battery as the battery case. For example, programmable pulse voltages may be provided by utilizing a microprocessor controlled digital to analog converter that would then control the output pulse voltages supplied at terminal 642 and 643. As another example, to allow short atrial-ventricular delays, the capacitor C1 and switches SW1 and SW2 may be repeated to provide separate atrial and ventricular negative pulse power sources. Other features may be added that are provided in existing pacemakers, defibulators and other types of implanted medical devices.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. A method for providing a leadless implantable medical device (LIMD) configured to be implanted within a local chamber of the heart, said method comprising:

forming a housing from a battery and an end cap, the battery having a battery case with a distal end and a terminal end, the end cap having a mating end and a proximal end, the proximal end of the end cap forming an LIMD proximal end and the distal end of the battery case forming an LIMD distal end;

mechanically securing the terminal end of the battery case to the mating end of the end cap with a non-conductive coupler, while maintaining the battery case and end cap electrically separated from one another;

joining a first electrode to the proximal end of the end cap, the first electrode oriented to project from the LIMD proximal end and configured to engage tissue at a first activation site; and attaching a second electrode that is electrically connected to the battery case, in a manner that the battery case forms part of a circuit that connects the second electrode to tissue at a second activation site.

2. The method of claim 1, further comprising utilizing the first and second electrodes to perform at least one of sensing and therapy delivery under control of an electronics module within an internal cavity of the end cap, and connecting first and second terminals of the battery to the electronics module such that the first terminal is electrically common with the battery case and the second electrode.

3. The method of claim 1, further comprising utilizing the end cap as a common electrode and delivering therapy to tissue between the second electrode and the end cap with the second electrode forming a cathode and the end cap forming an anode.

4. The method of claim 1, further comprising utilizing the end cap as a common electrode and delivering therapy to tissue between the first electrode and the end cap with the first electrode forming a cathode and the end cap forming an anode.

5. The method of claim 1, further comprising providing a charge storage unit having anode and cathode terminals, and connecting the cathode terminal to the battery case and first electrode when delivering therapy to the first activation site.

6. The method of claim 1, further comprising providing a charge storage unit having anode and cathode terminals, connecting the cathode terminal to the battery case and first electrode, and connecting the anode terminal to the end cap when delivering therapy to the first activation site.

7. The method of claim 1, further comprising surrounding the battery case with an insulation coating to isolate the battery case electrically from heart tissue.

8. The method of claim 1, further comprising directly connecting the battery case to the second electrode located distal from the LIMD by a wire.

9. The method of claim 1, wherein the non-conductive coupler has opposed edges that are bonded to, and electrically isolate, the battery case and the end cap, the battery case being electrically common with the second electrode and forming a cathode during therapy delivery.

10. The method of claim 1, wherein the non-conductive coupler constitutes one of a sapphire, ceramic or other hermetic electrically insulating material that is ring shaped and has opposed circumferential edges that are bonded to corresponding edges on the terminal end of the battery case and the mating end of the end cap.

* * * * *